United States Patent [19]

Bannell et al.

[11] Patent Number: 4,799,235
[45] Date of Patent: Jan. 17, 1989

[54] APPARATUS FOR MEASURING DEW-POINT OF A GAS STREAM WITH LIGHT SCATTERING

[75] Inventors: John L. K. Bannell; Arnold G. Dixon; Trevor P. Davies, all of Chester, England

[73] Assignee: Shell Oil Company, Houston, Tex.

[21] Appl. No.: 872,570

[22] Filed: Jun. 10, 1986

[30] Foreign Application Priority Data

Jun. 18, 1985 [GB] United Kingdom ............... 8514584

[51] Int. Cl.[4] .................................. G01N 25/68
[52] U.S. Cl. ............................ 374/18; 356/337; 374/27
[58] Field of Search ............... 374/16, 17, 20, 19, 374/18, 27; 356/337, 339

[56] References Cited

U.S. PATENT DOCUMENTS

| | | | |
|---|---|---|---|
| 3,166,928 | 1/1965 | Jackson et al. | 374/20 |
| 3,528,278 | 9/1970 | Sterling | 374/18 |
| 3,552,186 | 1/1971 | Sproul | 374/21 |
| 3,623,356 | 11/1971 | Bisberg . | |
| 3,812,596 | 5/1974 | Wilmanns | 34/51 |
| 3,890,828 | 6/1975 | Pleva | 73/29 |
| 4,083,224 | 4/1978 | Gayst | 374/19 |
| 4,328,455 | 5/1982 | Harding . | |
| 4,335,597 | 6/1982 | Hayes, Jr. et al. . | |
| 4,377,001 | 3/1983 | Takeda et al. | 374/17 |
| 4,589,274 | 5/1986 | Boyle et al. | 73/29 |
| 4,602,870 | 7/1986 | Rummel | 374/16 |
| 4,629,333 | 12/1986 | Dosoretz et al. | 374/20 |
| 4,701,052 | 10/1987 | Schoen, Jr. | 374/19 X |

FOREIGN PATENT DOCUMENTS

| | | |
|---|---|---|
| 2104499 | 8/1972 | Fed. Rep. of Germany . |
| 3243320 | 5/1984 | Fed. Rep. of Germany . |
| 58-7550 | 1/1983 | Japan .................. 374/17 |
| 2121960 | 1/1984 | United Kingdom .......... 356/337 |

OTHER PUBLICATIONS

"Advances in Instrumentation," vol. 37, Part 3, Proceedings of the ISA International Conference & Exhibit, Philadelphia, PA, Oct. 18-21, 1982.

Primary Examiner—Daniel M. Yasich

[57] ABSTRACT

An apparatus for measuring dew-point of a gas stream includes a sensor cell having a probe, means for cooling the probe, means for transmitting light to the probe surface in a pressurized chamber, means for receiving returned light scattered from the cooled probe surface, and means for determining dew-point from a reduction in scattered light intensity. The probe surface is provided in its center with a depression of low angle.

25 Claims, 2 Drawing Sheets

APPARATUS FOR MEASURING DEW-POINT OF A GAS STREAM WITH LIGHT SCATTERING

BACKGROUND OF THE INVENTION

The present invention relates to an apparatus for detecting dew-point of a gas stream or changes in the dew-point properties of a gas.

A variety of devices (for example, as shown in U.S. Pat. No. 3,812,596, issued May 28, 1974 to Wilmanns) based upon the principle of detecting the presence of dew on a cooled surface, for example a mirror, by means of light reflection techniques, are currently available for the determination of the water dew-point of gas streams, particularly humid air streams. However, their performance is not always as reliable and accurate as might be desired. Humid air is essentially a two-component mixture consisting of a single condensable component in, for all practical purposes, an incondensable carrier. Dew-point in such a mixture is therefore easily defined. However, many gas streams, such as those found in the onshore and offshore gas industry, and in gas processing and industrial plants, are often complex mixtures for which the dew-point is less readily defined. Such a mixture can be regarded as a series of condensable fractions, and dew-point is then defined as that temperature, at fixed pressure (or vice versa), when measurable dew can be detected. Further decrease in temperature will increase the amount of dew formed as more of the heavier fractions first condense. It has been found that quantities of heavier fractions present in small, but still analytically significant, quantities have a profound influence on the dew-point of such a mixture. No reliable automatic dew-point meter or monitor that can respond sensitively and accurately to the formation of the first significant condensation of such heavier components, which define the dew-point, is believed to be available.

In order to obtain an accurate indication of the dew-point it is necessary to meet predetermined requirements as to temperature and pressure and it will be necessary to present a gas sample to be investigated under controlled conditions to the detector.

The most successful of current devices for complex mixtures of gases are those based on the visual observation of dew on a cooled plane-mirror surface. Their sensitivity is poor, however, and the observation and interpretation of visual dew formation is subjective and susceptible to operator bias or mis-reading.

Initial work using this principle, but with electronic detection of the change in light reflectance, showed that the signal obtained was noisy, transient and unreliable. Condensed water is relatively easy to detect as it condenses in a drop-wise manner, but complex mixtures of gases condense with much lower contact angles and quickly form a film on the surface, thus restoring reflection.

SUMMARY OF THE INVENTION

It is thus an object of the present invention to provide an apparatus for detecting dew-point of gas streams which gives reliable and reproducible results.

The present invention therefore provides an apparatus for measuring dew-point of a gas stream. The apparatus includes a sensor cell which comprises a probe, means for transmitting light to the probe surface in a pressurized chamber, and means for receiving returned light scattered from the cooled probe surface. The apparatus further includes means for determining dew-point from a reduction in the scattered light intensity. Also, the probe surface in its center is provided with a depression of low angle. In one embodiment of the invention the depression is circular. In another embodiment the circular depression has a V-shape in cross section.

The invention is thus based upon detecting formation of dew on a cooled probe surface by the reduction in scattered light intensity from the surface when dew is present.

BRIEF DESCRIPTION OF THE DRAWINGS

The invention will now be described by way of example in more detail with reference to the accompanying drawings in which.

DESCRIPTION OF THE PREFERRED EMBODIMENTS

Figure 1:
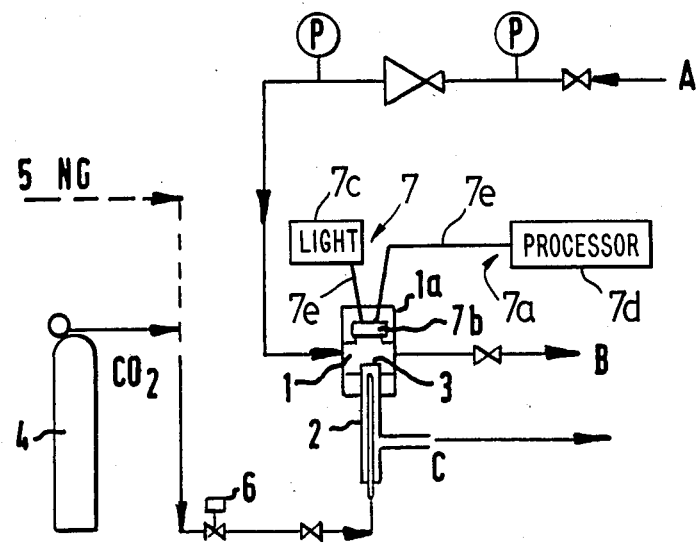
FIG. 1 represents a flow scheme of an apparatus for detecting dew-point of a gas stream, based upon detecting dew-point by the reduction in scattered light intensity from the probe surface when dew is present.

With reference to FIG. 1, a gas sample is taken from a flow line (not shown for reasons of clarity) at point A and flows continuously through the pressurized chamber 1 of a sensor cell 1a at a controlled pressure and flow rate.

The sensor cell 1a is provided with a probe 2.

Coolant gas (for example $CO_2$ from a storage vessle 4, but other suitable gases such as natural gas 5 shown in dashed lines could be considered) is expanded at a controlled rate to cool the probe surface 3, which is lightly abraded. The coolant gas is switched on/off cyclically with an air-actuated valve 6. It will be appreciated that the flows of sample gas and coolant gas are not critical. After passing the sensor cell the gas sample is processed further at B in any way suitable for the purpose. The used coolant flows through the outlet C of the probe assembly 2 and is processed further in any suitable manner.

In an alternative embodiment the sample gas flow may be interrupted in any way suitable for the purpose to trap a volume of gas in the sensor chamber 1.

Figure 2:
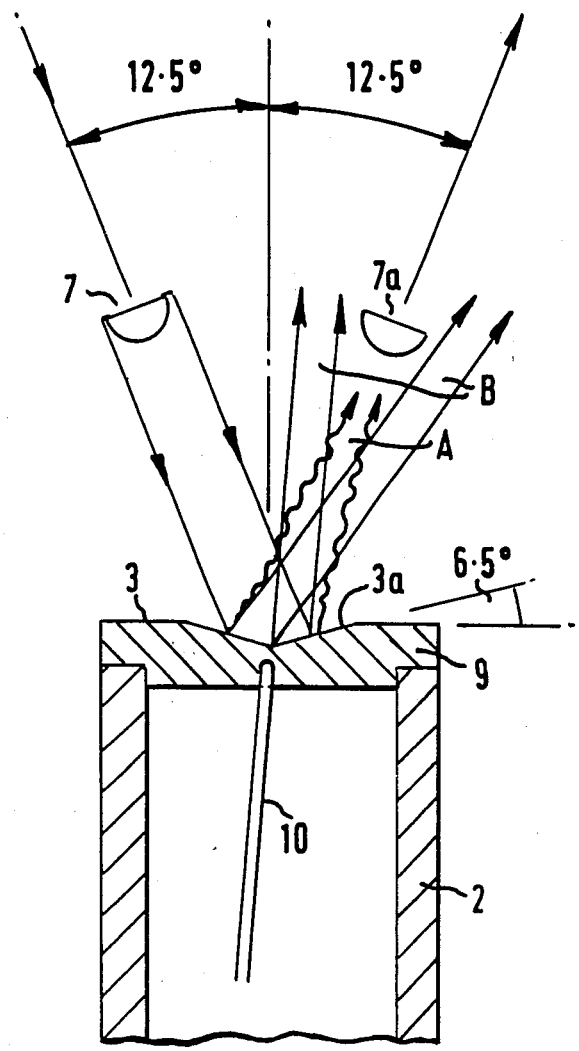
FIG. 2 illustrates the light scattering principle involved.

FIG. 2 represents diagrammatically part of a longitudinal section through the probe 2 and sample chamber 1 of the sensor cell 1a. A means for transmitting light such as light transmitting element 7 and a means for receiving returned light such as light collecting element 7a are arranged to have near coincident focus through window 7b (not shown for clarity in FIG. 2, but shown in FIG. 1) on the probe surface 3. However, the probe surface 3 is arranged to deflect light from a direct path between the transmiting element 7 and collecting element 7a. For the most part only light scattered by the probe surface 3 to the element 7a will be collected (represented as light beam A) whereas directly reflected light beams are steered away from the receiver (beams B). The probe surface 3 may be in the form of a circular conical depression 3a or extension in form. However, its angle and form are not critical provided these main deflection requirements are met. After machining and polishing, the conical depression 3a in the probe surface 3 is slightly roughened by mechanical, chemical, or other means to enhance the scattering of light from the surface.

Figure 3:
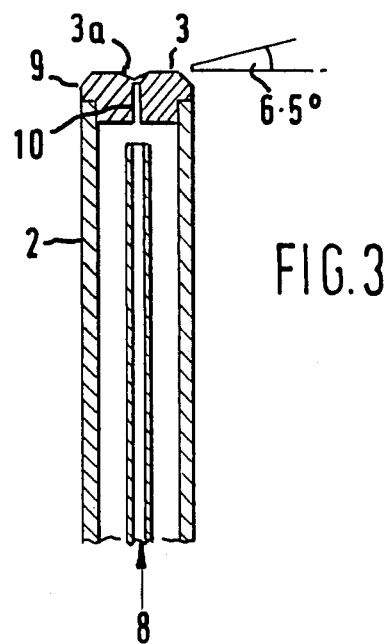
FIG. 3 represents a detail of FIGS. 1 and 2.

In an advantageous embodiment of this principle, as in FIGS. 2 and 3, the transmitting element 7 and collecting element and 7a are arranged at a half-angle of 10°–15°, and more in particular 12.5°, from the center line in combination with a 'V'-shaped circular depression of low angle. In advantageous embodiments this angle is 4°–8°, and more in particular 6.5°. The nominal diameter of the depression at the surface is 6 mm, which is equivalent to a nominal depth, at the center, of 0.34 mm. The relative geometry of probe surface, transmitting element 7 and receiving element 7a, and the optical and mechanical properties of the viewing window 7b provide a compact arrangement of components fit for the purposes of the invention. The coolant supply to the surface 3 is represented by reference numeral 8 in FIG. 3.

In the preferred embodiment, the transmitting element 7 and receiving element 7a include of suitable fiber optics 7e. Further, light transmitting element 7 includes a light source 7c and light receiving element 7a includes received signal processing at signal processor 7d, this processing occurs remotely from the dew-point sensor cell.

As already described in the foregoing, the scattering of returning light from the probe surface 3a will change when dew is present due to cooling this surface and the reduction in scattered light intensity that occurs when dew is present is detected to determine dew-point.

For example, in one of the practical embodiments of the invention, employing a sensor cell with a safe working pressure of 200 bar, the nominal sample flow is <0.02 m$^3$(st)/h with cooling by $CO_2$ at nominal rates of <0.5 l/°C, 0.2 °C/s and with cycle time >2 min. It will be appreciated that the safe working pressure of the sensor assembly is determined solely by mechanical consideration and in no sense is a constraint on application of the principle of the invention at higher (or lower) pressures.

The probe 2 and the probe tip 9 may be made of any material suitable for the purpose and may be connected mechanically in any suitable manner. The probe is provided with any suitable means (not shown for reasons of clarity) for mechanical connection to the sensor cell 1a. Reference numeral 10 in FIGS. 2 and 3 indicates the plate for a thermocouple, which continuously measures the temperature of the probe surface.

It will be appreciated that an advantageous embodiment of the invention can be used for measuring dew-point of hydrocarbon gas streams.

Various modificatons of the invention will become apparent to those skilled in the art from the foregoing description and accompanying drawings. Such modifications are intended to fall within the scope of the appended claims.

What is claimed is:

1. An apparatus for measuring condensible components in a gas stream, said apparatus comprising:
   a sensor cell which includes a pressurized chamber, a probe having a reflective surface located within said pressurized chamber, said reflective surface having a slightly roughened finish which reflects scattered light when dry and diverts directly reflected light in the presence of condensate; a means for cooling at least the surface of said probe; a depression of low angle in said surface of said probe a means for transmitting light to said surface of said probe in said pressurized chamber; a means for receiving returned light scattered from said surface of said probe which is positioned to receive scattered light, but is substantially out of alignment with the path of directly reflected light; and a means for determining the presence of condensate as a predetermined function of the reduction in scattered light intensity from said surface.

2. The apparatus as claimed in claim 1, wherein said depression is circular.

3. The apparatus as claimed in claim 2, wherein said depression has a V-shape in cross section.

4. The apparatus as claimed in claim 3, wherein the angle of said depression is 4°–8°.

5. The apparatus as claimed in claim 4, wherein the angle of said depression is 6.5°.

6. The apparatus as claimed in claim 3, wherein the depression has a nominal depth of 0.34 mm and a nominal diameter of 6 mm.

7. The apparatus as claimed in claim 1, wherein the half-angle between said means for transmitting light and said means for receiving light is 10°–15°.

8. The apparatus as claimed in claim 7, wherein said half-angle between said means for transmitting light and said means for receiving light is 12.5°.

9. The apparatus as claimed in claim 1 wherein the reflective surface has a roughened texture.

10. A method for measuring condensible components of a gas stream, comprising:
    cooling at least a surface of a probe located within a pressurized chamber in a sensor cell, the probe having a depression of low angle in the cooled surface thereof and the surface having a slightly roughened finish which reflects scattered light when dry and directly reflects light in the presence of condensate;
    providing a light source;
    transmitting light to the cooled surface of the probe in the pressurized chamber;
    receiving reflected light scattered from the cooled surface of the probe at a light receiving element which is positioned substantially out of alignment with the path of the directly reflected light; and
    determining the presence of condensate as a predetermined function of the reduction in scattered light intensity from the cooled surface of the probe.

11. The method as claimed in claim 10, wherein the depression is circular.

12. The method as claimed in claim 11, wherein the depression has a V-shape in cross section.

13. The method as claimed in claim 12, wherein the angle of the depression is 4+–8°.

14. The method as claimed in claim 13, wherein the angle of the depression is 6.5°.

15. The method as claimed in claim 12, wherein the V-shaped depression has a nominal depth of 0.34 mm and a nominal diameter of 6 mm.

16. The method as claimed in claim 10, wherein the half-angle between the transmitted light and the received light is 10°–15°.

17. The methods as claimed in claim 16, wherein the half-angle between the transmitted light and the received light is 12.5°.

18. An apparatus for measuring the hydrocarbon dew-point of a gas stream, said apparatus comprising:
    a sensor cell which includes a pressurized chamber, a probe having a reflective surface located within said pressurized chamber, said reflective surface having a slightly roughened finish which reflects scattered light when dry and diverts directly reflected light in the presence of condensate; a means for cooling at least the surface of said probe; a depression of low angle in said surface of said probe; a means for transmitting light to said surface of said probe in said pressurized chamber; means for receiving returned light scattered from said surface of said probe which is positioned to receive scattered light but is substantially out of alignment with the path of directly reflected light; and a means for determining the hydrocarbon dew-point as a predetermined function of the reduction in scattered light intensity from said surface.

19. A method for measuring the hydrocarbon dew-point of a gas stream, comprising:

cooling at least a surface of a probe located within a pressurized chamber in a sensor cell, the probe having a depression of low angle in a portion of the cooled surface thereof and the surface having a finish which reflects scattered light when dry and directly reflects light in the presence of condensate;

providing a light source;

transmitting light to the cooled surface of the probe in the pressurized chamber;

receiving reflected light scattered from the cooled surface of the probe at a light receiving element which is positioned substantially out of alignment with the path of the directly reflected light; and determining the hydrocarbon dew-point as a predetermined function of the reduction in scattered light intensity from the cooled surface of the probe.

20. An apparatus for measuring condensible components in a gas stream, said apparatus comprising:

a sensor cell comprising:

a pressurized chamber;

a probe having a slightly roughened reflective surface located within the pressurized chamber;

a circular depression having a low angle V-shaped cross section formed on the surface of the probe;

a means for transmitting light to the surface of the probe in said pressurized chamber;

a means for receiving returned light scattered from the surface of the probe; and a means for determining the presence of condensate as a predetermined function of the reduction in scattered light intensity from said surface.

21. The apparatus as claimed in claim 20, wherein the angle of said depression is 4°–8°.

22. The apparatus as claimed in claim 21, wherein the angle of said depression is 6.5°.

23. The apparatus as claimed in claim 20, wherein the depression has a nominal depth of 0.34 mm and a nominal diameter of 6 mm.

24. The apparatus as claimed in claim 20, wherein the half-angle between said means for transmitting light and said means for receiving light is 10°–15°.

25. The apparatus as claimed in claim 24, wherein said half-angle between said means for transmitting light and said means for receiving light is 12.5°.

* * * * *